US00PP31557P2

(12) United States Plant Patent
Magee

(10) Patent No.: US PP31,557 P2
(45) Date of Patent: Mar. 17, 2020

(54) CRAPEMYRTLE PLANT NAMED 'JM5'

(50) Latin Name: ***Lagerstroemia indica* 'JM5'**
Varietal Denomination: JM5

(71) Applicant: Jack Mitchell Magee, Poplarville, MS (US)

(72) Inventor: Jack Mitchell Magee, Poplarville, MS (US)

(73) Assignees: Greenleaf Nursery Company, Park Hill, OK (US); Evergreen Nursery, Poplarville, MS (US)

( * ) Notice: Subject to any disclaimer, the term of this patent is extended or adjusted under 35 U.S.C. 154(b) by 0 days.

(21) Appl. No.: 16/350,175

(22) Filed: Oct. 10, 2018

(51) Int. Cl.
*A01H 5/00* (2018.01)

(52) U.S. Cl.
USPC ..... Plt./252

(58) Field of Classification Search
USPC ..... Plt./252
CPC ..... A01H 5/00
See application file for complete search history.

*Primary Examiner* — Annette H Para
(74) *Attorney, Agent, or Firm* — C. A. Whealy

(57) ABSTRACT

A new and distinct cultivar of Crapemyrtle plant named 'JM5', characterized by its upright to somewhat outwardly spreading plant habit; freely branching habit; vigorous and sturdy growth habit; leaves that are dark greyed purple in color; numerous inflorescences with light red purple-colored flowers; and good garden performance and pathogen resistance.

2 Drawing Sheets

Botanical designation: *Lagerstroemia indica* 'JM5'.
Cultivar denomination: 'JM5'.

CROSS-REFERENCED TO CLOSELY-RELATED APPLICATIONS

Title: Crapemyrtle Plant Named 'JM1'
Applicant: Jack Mitchell Magee
U.S. Plant patent application Ser. No. 16/350,178
Title: Crapemyrtle Plant Named 'JM3'
Applicant: Jack Mitchell Magee
U.S. Plant patent application Ser. No. 16/350,180
Title: Crapemyrtle Plant Named 'JM4'
Applicant: Jack Mitchell Magee
U.S. Plant patent application Ser. No. 16/350,179

BACKGROUND OF THE INVENTION

The present invention relates to a new and distinct cultivar of Crapemyrtle plant, botanically known as *Lagerstroemia indica* 'JM5' and hereinafter referred to by the name 'JM5'.

The new Crapemyrtle plant is a product of a planned breeding program conducted by the Inventor in Poplarville, Miss. The objective of the breeding program was to develop new vigorous and freely-branching Crapemyrtle plants with dark-colored leaves and attractive flower colors.

The new Crapemyrtle plant originated from a cross-pollination conducted by the Inventor during the summer of 2015 of *Lagerstroemia indica* 'Natchez White', not patented, as the female, or seed, parent with *Lagerstroemia indica* 'Ebony Flame', not patented, as the male, or pollen, parent. The new Crapemyrtle plant was discovered and selected by the Inventor in May, 2016 as a single flowering plant from within the progeny of the stated cross-pollination in a controlled nursery environment in Poplarville, Miss.

Asexual reproduction of the new Crapemyrtle plant by vegetative softwood cuttings in a controlled greenhouse environment in Poplarville, Miss. since August, 2016 has shown that the unique features of the new Crapemyrtle plant are stable and reproduced true to type in successive generations of asexual reproduction.

SUMMARY OF THE INVENTION

Plants of the new Crapemyrtle have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'JM5'. These characteristics in combination distinguish 'JM5' as a new and distinct Crapemyrtle plant:

1. Upright to somewhat outwardly spreading plant habit.
2. Freely branching habit.
3. Vigorous and sturdy growth habit.
4. Leaves that are dark greyed purple in color.
5. Numerous inflorescences with light red purple-colored flowers.
6. Good garden performance and pathogen resistance.

Plants of the new Crapemyrtle can be compared to plants of the female parent, 'Natchez White'. Plants of the new Crapemyrtle differ primarily from plants of 'Natchez White' in the following characteristics:

1. Plants of the new Crapemyrtle have dark greyed purple-colored leaves whereas plants of 'Natchez White' have light green-colored leaves.
2. Plants of the new Crapemyrtle have light red purple-colored flowers whereas plants of 'Natchez White' have white-colored flowers.

Plants of the new Crapemyrtle can be compared to plants of the male parent, 'Ebony Flame'. Plants of the new Crapemyrtle differ primarily from plants of Ebony Flame in the following characteristics:

1. Plants of the new Crapemyrtle are larger and more vigorous than plants of 'Ebony Flame'.
2. Plants of the new Crapemyrtle have light red purple-colored flowers whereas plants of 'Ebony Flame' have red-colored flowers.

Plants of the new Crapemyrtle can be compared to plants of *Lagerstroemia indica* 'JM1', disclosed in U.S. Plant patent application Ser. No. 16/350,178. Plants of the new Crapemyrtle differ primarily from plants of 'JM1' in the following characteristics:

1. Plants of the new Crapemyrtle have dark greyed purple-colored leaves whereas plants of 'JM1' have dark green-colored leaves.
2. Plants of the new Crapemyrtle have light red purple-colored flowers whereas plants of 'JM1' have dark red-colored flowers.

Plants of the new Crapemyrtle can be compared to plants of *Lagerstroemia indica* 'JM3', disclosed in U.S. Plant patent application Ser. No. 16/350,180. Plants of the new Crapemyrtle differ primarily from plants of 'JM3' in the following characteristics:

1. Plants of the new Crapemyrtle have dark greyed purple-colored leaves whereas plants of 'JM3' have dark purple-colored leaves.
2. Plants of the new Crapemyrtle have light red purple-colored flowers whereas plants of 'JM3' have light purple-colored flowers.

Plants of the new Crapemyrtle can also be compared to plants of *Lagerstroemia indica* 'JM4', disclosed in U.S. Plant patent application Ser. No. 16/350,179. Plants of the new Crapemyrtle differ primarily from plants of 'JM4' in the following characteristics:

1. Plants of the new Crapemyrtle have dark greyed purple-colored leaves whereas plants of 'JM4' have green-colored leaves.
2. Plants of the new Crapemyrtle have light red purple-colored flowers whereas plants of 'JM4' have white-colored flowers.

Plants of the new Crapemyrtle can be compared to plants of the *Lagerstroemia indica* 'Bradberry's Wine', disclosed in U.S. Plant Pat. No. 20,926. In side-by-side comparisons, plants of the new Crapemyrtle differ primarily from plants of 'Bradberry's Wine' in the following characteristics:

1. Plants of the new Crapemyrtle are more vigorous and faster growing than plants of 'Bradberry's Wine'.
2. Plants of the new Crapemyrtle have dark greyed purple-colored leaves whereas plants of 'Bradberry's Wine' have dark green-colored leaves.
3. Plants of the new Crapemyrtle have light red purple-colored flowers whereas plants of 'Bradberry's Wine' have darker red purple-colored flowers.

Plants of the new Crapemyrtle can be compared to plants of the *Lagerstroemia indica* 'Tuscarora', not patented. In side-by-side comparisons, plants of the new Crapemyrtle differ primarily from plants of 'Tuscarora' in the following characteristics:

1. Plants of the new Crapemyrtle are more vigorous and grow faster than plants of 'Tuscarora'.
2. Plants of the new Crapemyrtle have dark greyed purple-colored leaves whereas plants of 'Tuscarora' have dark green-colored leaves.
3. Plants of the new Crapemyrtle have light red purple-colored flowers whereas plants of 'Tuscarora' have coral-colored flowers.
4. Plants of the new Crapemyrtle are more pathogen-resistant than plants of 'Tuscarora'.

BRIEF DESCRIPTION OF THE PHOTOGRAPHS

The accompanying colored photographs illustrate the overall appearance of the new Crapemyrtle plant showing the colors as true as it is reasonably possible to obtain in colored reproductions of this type. Colors in the photographs may differ slightly from the color values cited in the detailed botanical description which accurately describe the colors of the new Crapemyrtle plant.

The photograph on the first sheet is a side perspective view of a typical plant of 'JM5' grown in a container in an outdoor nursery.

The photograph on the second sheet is a close-up view of a typical flowering plant of 'JM5' grown in a container in an outdoor nursery.

DETAILED BOTANICAL DESCRIPTION

The aforementioned photographs and following observations, measurements and values describe plants grown in 7-gallon containers in Park Hill, Okla. and Fort Worth, Tex. during the summer in outdoor nurseries and under cultural conditions which closely approximate commercial Crapemyrtle production. During the production of the plants, day temperatures averaged 33° C. and night temperatures averaged 14° C. Plants were three years when the photographs and the description were taken. In the following description, color references are made to The Royal Horticultural Society Colour Chart, 2015 Edition, except where general terms of ordinary dictionary significance are used.

Botanical classification: *Lagerstroemia indica* 'JM5'.

Parentage:

*Female, or seed, parent.*—*Lagerstroemia indica* 'Natchez White', not patented.

*Male, or pollen, parent.*—*Lagerstroemia indica* 'Ebony Flame', not patented.

Propagation:

*Type.*—By vegetative softwood and hardwood cuttings.

*Time to initiate roots, summer.*—About ten days at temperatures about 21° C. to 33° C.

*Time to initiate roots, winter.*—About 25 days at temperatures about 21° C. to 33° C.

*Time to produce a rooted young plant, summer.*—About one month at temperatures about 21° C. to 33° C.

*Time to produce a rooted young plant, winter.*—About one month for softwood cuttings and about two months for hardwood cuttings at temperatures about 21° C. to 33° C.

*Root description.*—Medium in thickness, fibrous; typically brownish white in color, actual color is dependent on substrate composition, water quality, fertilizer type and formulation, substrate temperature and physiological age of roots.

*Rooting habit.*—Freely branching; dense.

Plant description:

*Plant form and growth habit.*—Perennial shrub; upright to somewhat outwardly spreading plant habit; vigorous and sturdy growth habit.

*Branching habit.*—Freely branching habit with about seven to eight primary lateral branches each with numerous secondary and tertiary lateral branches developing per plant.

*Plant height*.—About 157 cm.

*Plant diameter* (*area of spread*).—About 91 cm.

Lateral branch description:

*Length*.—About 155 cm.

*Diameter, at soil level*.—About 1.5 cm.

*Internode length*.—About 1.5 cm to 2 cm.

*Strength*.—Strong.

*Aspect*.—About 25° to 40° from vertical.

*Texture*.—Smooth, glabrous; woody with age.

*Color, immature*.—Close to 187A.

*Color, mature*.—Close to 177A to 177B.

*Color, mature at the base of the plant*.—Close to 199A.

Leaf description:

*Arrangement*.—Alternate; simple.

*Length*.—About 5.2 cm.

*Width*.—About 3.4 cm.

*Shape*.—Ovate.

*Apex*.—Acute to cuspidate.

*Base*.—Obtuse.

*Margin*.—Entire.

*Texture and luster, upper and lower surfaces*.—Smooth, glabrous; somewhat glossy.

*Venation pattern*.—Pinnate.

*Color*.—Developing leaves, upper surface: Close to 147A. Developing leaves, lower surface: Close to 146A to 146B. Fully expanded leaves, upper surface: Close to N186A; venation, close to 187A; autumnal color, close to 185A. Fully expanded leaves, lower surface: Close to between 147A and 147B variably tinged with close to 187A to 187B; venation, close to 144A; autumnal color, close to 183A to 183B.

*Petioles*.—Length: About 3 mm. Diameter: About 2 mm. Texture and luster, upper and lower surfaces: Smooth, glabrous; somewhat glossy. Color, upper surface: Close to 146A. Color, lower surface: Close to 144A.

Flower description:

*Flower type, arrangement and habit*.—Showy single ruffled flowers arranged in terminal panicles; freely flowering habit with usually about 36 to 52 flowers per inflorescence and numerous inflorescences developing during the flowering season; flowers face upright and outwardly depending on the flower's position on the panicle; flowers not persistent.

*Natural flowering season*.—Plants of the new Crapemyrtle flower from the mid-summer until the autumn in Park Hill, Okla.

*Fragrance*.—None detected.

*Inflorescence height*.—About 15 cm.

*Inflorescence diameter*.—About 8 cm.

*Flower length*.—About 4 cm.

*Flower diameter*.—About 4 cm.

*Flower depth*.—About 2 cm.

*Flower buds*.—Length: About 8 mm. Diameter: About 7 mm. Shape: Obovate. Texture and luster: Smooth, glabrous; moderately glossy. Color: Close to between 144A and 146A.

*Petals*.—Quantity per flower and arrangement: Six arranged in a single whorl. Length: About 2 cm. Width: About 1.5 cm. Shape: Roughly orbicular. Apex: Rounded, undulate and ruffled. Base: Rounded and fused into a slender tube. Margin: Entire, undulate and ruffled. Texture and luster, upper and lower surfaces: Smooth, glabrous; soft and delicate; matte. Color: When opening, upper and lower surfaces: Close to between 57C to 57D and 61D. Fully opened, upper and lower surfaces: Close to between 57C to 57D and 61D; color becoming closer to 62A to 62B with development.

*Sepals*.—Quantity per flower and arrangement: Six arranged in a single whorl. Length: About 1.1 cm. Width: About 5 mm. Shape: Obovate. Apex: Acute. Base: Attenuate, fused. Margin: Entire. Texture and luster, upper and lower surfaces: Smooth, glabrous; moderately glossy. Color: When opening and fully opened, upper surface: Close to 145C. When opening and fully opened, lower surface: Close to between 144A and 146A.

*Pedicels*.—Length: About 2 cm. Diameter: About 2.5 mm. Strength: Strong, flexible. Aspect: About 45° to 50° from stem axis. Texture and luster: Smooth, glabrous; somewhat glossy. Color: Close to 144A.

*Reproductive organs*.—Androecium: Quantity per flower: About 24. Filament length: About 8 mm. Filament color: Close to NN155D. Anther length: About 1 mm. Anther shape: Oblong. Anther color: Close to 9A. Amount of pollen: None observed. Gynoecium: Quantity per flower: Six, one per petal. Pistil length: About 1.8 cm. Style length: About 1.6 cm. Style color: Close to 144B to 144C. Stigma appearance: Rounded. Stigma color: Close to 144A. Ovary: Close to 154D.

*Fruits and seeds*.—To date, fruit and seed development has not been observed on plants of the new Crapemyrtle.

Garden performance: Plants of the new Crapemyrtle have been observed to have good garden performance and to tolerate rain, wind and temperatures ranging from about −10° C. to about 38° C. and to be cold hardy to USDA Hardiness Zone 6.

Pathogen & pest resistance: Plants of the new Crapemyrtle have been observed to be resistant to leaf spot (*Cercospora lythracearum*) and powdery mildew (*Erysiphe lagerstroemia*). Plants of the new Crapemyrtle have not been observed to be resistant to pests and other pathogens common to Crapemyrtle plants.

It is claimed:

1. A new and distinct Crapemyrtle plant named 'JM5' as illustrated and described.

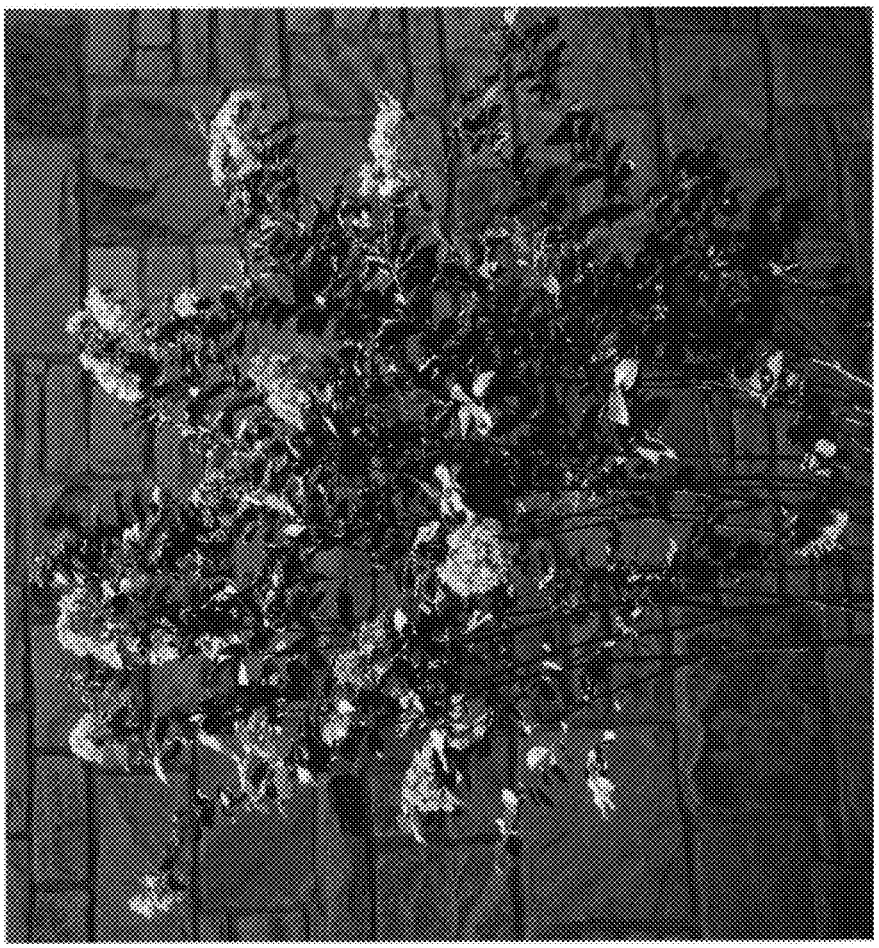

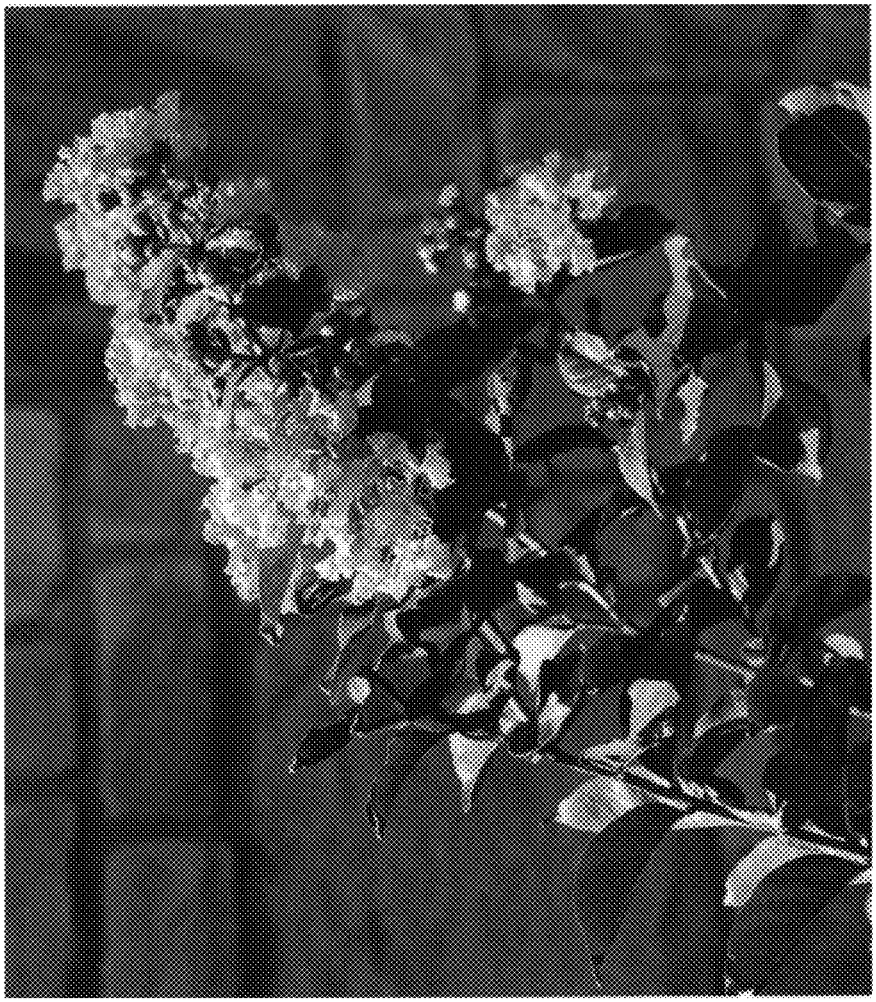

* * * * *